United States Patent
Morales

(10) Patent No.: US 7,309,275 B1
(45) Date of Patent: Dec. 18, 2007

(54) THERAPEUTIC BRASSIERE INCORPORATING THERMAL GEL

(76) Inventor: James Morales, 5921 Grass Creek Dr., Bakersfield, CA (US) 93311

( * ) Notice: Subject to any disclaimer, the term of this patent is extended or adjusted under 35 U.S.C. 154(b) by 49 days.

(21) Appl. No.: 11/220,305

(22) Filed: Sep. 6, 2005

(51) Int. Cl.
*A41C 3/10* (2006.01)
*A41C 3/12* (2006.01)

(52) U.S. Cl. .......................... 450/38; 450/54; 450/58; 607/114

(58) Field of Classification Search ............ 450/36–38, 450/54–58; 2/102; 607/109–114, 106–107
See application file for complete search history.

(56) References Cited

U.S. PATENT DOCUMENTS

| | | | |
|---|---|---|---|
| 2,298,361 A | | 10/1942 | Freund |
| 4,585,003 A | | 4/1986 | Meistrell |
| 5,050,595 A | | 9/1991 | Krafft |
| 5,235,974 A | | 8/1993 | Miller |
| 5,304,215 A | * | 4/1994 | MacWhinnie et al. ...... 607/108 |
| 5,427,563 A | * | 6/1995 | Manning ..................... 450/79 |
| 5,679,052 A | * | 10/1997 | Rucki .......................... 450/57 |
| 5,776,177 A | * | 7/1998 | MacWhinnie et al. ...... 607/108 |
| 5,839,942 A | * | 11/1998 | Miller .......................... 450/58 |
| 6,063,110 A | | 5/2000 | Stedman |
| 6,241,715 B1 | * | 6/2001 | Houser et al. ......... 604/385.07 |
| 6,261,313 B1 | * | 7/2001 | MacWhinnie et al. ...... 607/108 |
| 6,394,879 B1 | * | 5/2002 | Paige .......................... 450/38 |
| 6,464,717 B1 | * | 10/2002 | Smith et al. ................. 607/108 |

FOREIGN PATENT DOCUMENTS

| | | |
|---|---|---|
| CA | 2.280.456 | 2/2001 |
| GB | 2.093.350 | 9/1982 |
| WO | WO94/14392 | 7/1994 |
| WO | WO00/76433 | 12/2000 |

* cited by examiner

*Primary Examiner*—Gloria M. Hale
(74) *Attorney, Agent, or Firm*—Michael I Kroll

(57) ABSTRACT

A brassiere incorporating at least one gel pack positioned to provide thermal therapy to a breast. Located within the breast cup construction are one or more cells of thermal gel packs designed to dispense thermal therapy to the breast, preferably cold therapy. The gel sac or sacs form an integral part of the garment sandwiched between layers of material forming the interior and exterior of the garment. The respective breast cup gel sac can be formed to partially or fully encompass the breast or segmented into a plurality of segregated sacs having padding positioned therebetween forming gel sac support. The garment closure means is easily moved between a worn engaged state and disengaged state for removal.

6 Claims, 10 Drawing Sheets

THERAPEUTIC BRASSIERE INCORPORATING THERMAL GEL

BACKGROUND OF THE INVENTION

1. Field of the Invention

The present invention relates generally to undergarments and, more specifically, to a brassiere incorporating at least one gel pack positioned to provide thermal therapy to a breast. The article of apparel forming an undergarment is designed with closure means positioned transversally between the breasts in the form of lengths of mating hook and loop fixed to the hem closure. A common strap laterally extends from the breast cups across the back serving as apparel hem with vertically extending straps from the rear across the shoulders terminating substantially at the breast cup apex with the strapsforming apertures whereby the user places their arms through the respective aperture and secures the bodice garment using the aforementioned frontally engaging mating lengths of hook and loop closure members.

Located within the breast cup construction is one or more cells of gel-like material designed to dispense thermal therapy to the breast, preferably cold therapy. The gel sac or sacs form an integral part of the garment sandwiched between layers of material forming the interior and exterior of the garment. The respective breast cup gel sac can be formed to partially or fully encompass the breast or segmented into a plurality of segregated sacs having padding positioned therebetween forming gel sac support. The garment closure means is easily moved between a worn engaged state and disengaged state for removal.

2. Description of the Prior Art

There are other garments device designed for thermal treatment. Typical of these is U.S. Pat. No. 2,298,361 issued to Freund on Oct. 13, 1942.

Another patent was issued to Meistrell on Apr. 29, 1986 as U.S. Pat. No. 4,585,003. Yet another U.S. Pat. No. 5,050,595 was issued to Krafft on Sep. 24, 1991 and still yet another was issued on Jun. 27, 1995 to Miller as U.S. Pat. No. 5,235,974.

Another patent was issued to Manning on Jun. 27, 1995 as U.S. Pat. No. 5,427,563. Yet another U.S. Pat. No. 6,063,110 was issued to Stedman on May 16, 2000. Another was issued to Paige on May 28, 2002 as U.S. Pat. No. 6,394,879 and still yet another was issued on Oct. 15, 2002 to Smith et al. as U.S. Pat. No. 6,464,717.

Another patent was issued to Godisan on Feb. 10, 2001 as Canadian Patent No. CA2,280,456. Yet another U.K. Patent No. GB2093350 was issued to Bechara, et al. on Sep. 2, 1982. Another was published to Deal, et al. on Dec. 21, 2000 as International Patent Application No. WO/0076433 and still yet another was published on Jul. 7, 1994 to Walker as International Patent Application No. WO94/14392

U.S. Pat. No. 2,298,361

Inventor: Elizabeth A. Freund

Issued: Oct. 13, 1942

Means for treating those portions of the female body containing the milk glands, comprising a rubber bag made in the shape of a brassiere and having elongated tapered and hollow end portions extending under the armpits, straps connected to the ends of the bag and extending around the back of the user, means for connecting the straps together, a pair of neck straps connected with the top part of the bag, means for connecting the neck straps together, said bag having a filling opening, a closure for the same, the front part of the bag having openings therein for the passage of the breasts, a pair of small substantially cup-shaped hollow bags adapted to cover the breasts, means for detachably connecting the small bags to the main bag around the openings in the main bag, each small bag having a filling opening and closure means for the same.

U.S. Pat. No. 4,585,003

Inventor: William R. Melstrell

Issued: Apr. 29, 1986

A heat or cold pack retention device comprises (a) elongated, insulative, flexible, relatively thin sheet means having two generally parallel, elongated legs joined to a sheet main portion, (b) said main portion provided with an anchor to anchor the pack, the sheet main portion then engaging and conforming to the shape of the pack, (c) the legs then being adapted to adjustably wrap about and over the same main portion and hold the pack to a user's body.

U.S. Pat. No. 5,050,595

Inventor: Pam Krafft

Issued: Sep. 24, 1991

A women's therapeutic support garment comprising a pair of breast supporting cups each of which is formed with an inner and an outer panel defining therebetween one of two cupped shaped pockets. A cupped shaped, thermal gel pack is placed in each pocket and has a central opening for accommodating the women's nipple. A pair of side panels are connected to the breast supporting cups, the side panels being dimensioned and configured to encircle the wearer and hold the breast supporting cups in place with the gel packs surrounding the women's breasts. The heat from each gel pack serves to reduce swelling and tenderness of the breast tissues during the premenstrual period, pregnancy or the post-partum period.

U.S. Pat. No. 5,235,974

Inventor: Darlene N. Miller

Issued: Aug. 17, 1993

A heated bra is arranged to relieve engorgement in a lactating mother, wherein the bra structure includes a heated wire member directed coextensively in surrounding relationship relative to each cup member in electrical communication with an electrical energy source. The bra structure is further arranged to include a fluid impermeable chamber to accommodate heated water and other fluids to assist in relieving pressure to an individual.

U.S. Pat. No. 5,427,563

Inventor: Judith W. Manning

Issued: Jun. 27, 1995

A breast wrap (10) has two rectangular non-stretching panels (11, 12) of cotton flannel material joined over a user's back by short elastic strips (16, 17), and joined in overlapping relationship across the breasts by upper and lower complementary hook-and-loop fasteners (28, 29, 30, 31) running marginally along upper and lower longitudinal edges (24, 25, 26, 27). The panels run lengthwise in opposite directions from the user's back, under one arm, across both breasts, and terminate at a point located under the other arm; the panels run widthwise from above the breasts to below the breasts; and the fasteners are located so they will not be pressed into the breasts. Two rectangular open-ended pouches (40, 41) having pockets (40) for crushed ice, are held between the overlapping panels by additional hook-and-loop fasteners (47, 48) that mate with fasteners (28, 29, 30, 31).

U.S. Pat. No. 6,063,110

Inventor: Veronica Mercia Stedman

Issued: May 16, 2000

The present invention relates to a device for the relief or treatment of painful or tender breasts in a lactating women comprising, a support attachable to a womens upper body and a breast cover mounted to said support for at least partially covering one or both breasts, whereby in use said breast cover induces localised heating or cooling in at least part of said one or both breasts.

U.S. Pat. No. 6,394,879

Inventor: Christine M. Paige

Issued: May 28, 2002

A postpartum brassiere for providing comfort to the breasts of a mother who does not breast feed. The postpartum brassiere includes a panel having an inner surface, an outer surface, a top edge, a bottom edge, a first side edge and a second side edge. A fastening member removably fastens the outer surface adjacent to the first side edge to the inner surface adjacent to the second side edge. The panel comprises a cloth material. The panel has a first section abutting the first side edge, a second section abutting the second side edge and a middle section positioned between the first and second sections. Each of a pair of pockets is attached to the inner surface of the panel and positioned on the middle section. Each of a pair of gel packs is positionable in one of the pockets.

U.S. Pat. No. 6,464,717

Inventor: Gairy L. Smith

Issued: Oct. 15, 2002

The bra with hot/cold inserts is a therapeutic device in the form of a vest-like elastic garment adapted to be worn on the human upper torso. The device includes front panels having pockets therein for retaining gel packs. The device is effective in providing warm or cold therapy to the chest and rib areas. The garment can be used by humans of both genders.

Canadian Patent Number CA2,280,456

Inventor: Rosalie Godisan

Issued: Feb. 10, 2001

The invention discloses a bra made from a terrycloth material without a neck strap.

U.K. Patent Number GB2093350

Inventor: Victoria Bechara, et al.

Issued: Sep. 2, 1982

A device for use in treating a part of the human body comprises in combination a sealed envelope (20) formed by a pair of membranes (30, 40) sealed together adjacent the peripheral edges (50, 51) thereof so as to form the envelope (20); and a quantity of liquid (60) and air (60a) in the envelope, so that the envelope remains pliable at room temperature, the liquid being introduced into the envelope prior to the final permanent sealing of the envelope to thereby provide a permanently sealed and permanently filled device (10). A method of heating or cooling a human female breast utilises the device in combination with a former which allows the nipple to protrude.

International Patent Application Number WO00/76433

Inventor: Ann Deal, et al.

Issued: Dec. 21, 2000

A push-up bra (10) has a sleeve between the front panel (20) and the rear panel (22) of the bra cups (12, 14) that receives a flexible pouch (38, 40) containing a body (42) of malleable material such as a major amount of a liquid polyol such as glycerine reacted with a vegetable starch, a small amount of a finely divided mineral such as AEROSIL as a suspending agent, a water scavenger such as magnesium oxide, a lightweight, water-soluble organic filler such as a cellulose ether and a water soluble preservative. The malleable material can be molded into a shape under and/or to either side of a breast to control the shape, amount of lift and the cleft between breasts.

International Patent Application Number WO94/14392

Inventor: Alfred M. Walker

Issued: Jul. 7, 1994

The present invention relates to a thermal heat pack (104) for heating the female breast during post partum nursing and, more particularly, to a thermal heat pack (104) which readily conforms to the contours of different sized female breasts to provide therapeutic heat to an adjacent breast to reduce swelling and irritation. The present invention overcomes the disadvantages of the prior art by providing a bendable thermal heat unit which assumes a cup or cone shape upon application to the breast. The present invention adjusts and conforms to various sizes of the female breasts to which it is to be applied. The present invention provides a layered conformable member with a shape substantially like a disk having selected indentations (101) to permit formation of various sized rounded conical cups.

While these garments may be suitable for the purposes for which they were designed, they would not be as suitable for the purposes of the present invention, as hereinafter described.

SUMMARY OF THE PRESENT INVENTION

A primary object of the present invention is to provide a brassiere incorporating means to apply thermal therapy to breasts.

Another object of the present invention is to provide a brassiere that is fastened with matable closure between the breasts.

Yet another object of the present invention is to provide a brassiere having a breast cup construction with an interior material layer and an exterior material layer with a gel sac fixed therebetween and forming an integral part therewith.

Still yet another object of the present invention is to provide a brassiere wherein said gel sac partially or completely encompasses the respective breast.

Another object of the present invention is to provide a brassiere wherein said partially encompassing gel sac employs padding radially extending from the periphery of the gel sac for a natural appearance.

Yet another object of the present invention is to provide a brassiere wherein said gel sac is segmented into a plurality of gel sac cells with padding material positioned therebetween forming additional support for the gel sacs.

Additional objects of the present invention will appear as the description proceeds.

The present invention overcomes the shortcomings of the prior art by providing a brassiere incorporating at least one gel pack positioned to provide thermal therapy to a breast. The article of apparel forming an undergarment is designed with closure means positioned transversally between the breasts in the form of lengths of mating hook and loop fixed to the hem closure. A common strap laterally extends from the breast cups across the back serving as apparel hem with vertically extending straps from the rear across the shoulders terminating substantially at the breast cup apex with the strapsforming apertures whereby the user places their arms through the respective aperture and secures the bodice garment using the aforementioned frontally engaging mating lengths of hook and loop closure members.

Located within the breast cup construction is one or more cells of gel-like material designed to dispense thermal therapy to the breast, preferably cold therapy. The gel sac or sacs form an integral part of the garment sandwiched between layers of material forming the interior and exterior of the garment. The respective breast cup gel sac can be formed to partially or fully encompass the breast or segmented into a plurality of segregated sacs having padding positioned therebetween forming gel sac support. The garment closure means is easily moved between a worn engaged state and disengaged state for removal.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
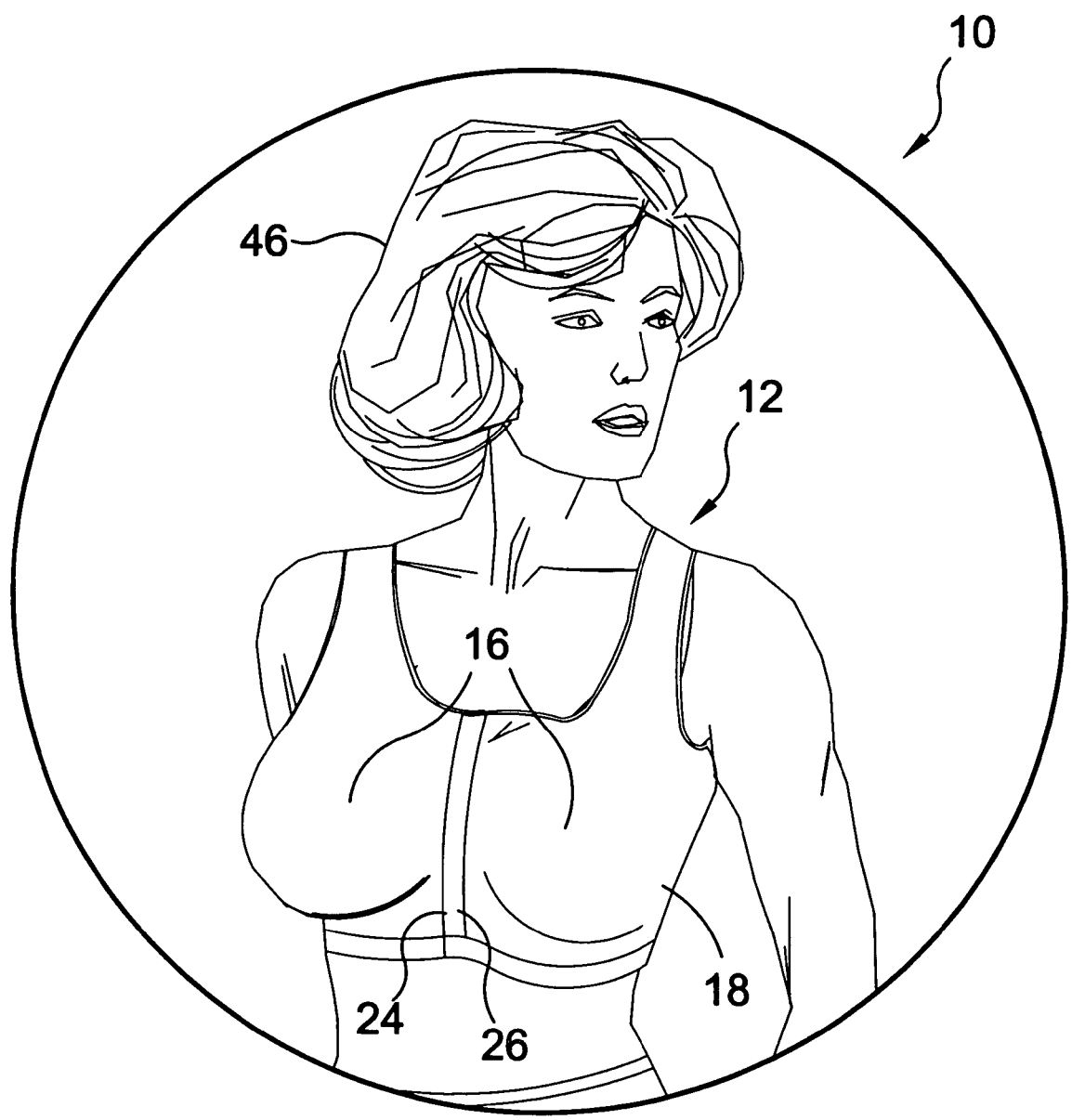
FIG. 1 is an illustrative view of the present invention in use.

Turning now descriptively to the drawings, in which similar reference characters denote similar elements throughout the several views, the figures illustrate the Therapeutic Brassiere Incorporating Thermal Gel Packs of the present invention. With regard to the reference numerals used, the following is used throughout the various drawing figures.

10 Therapeutic Brassiere Incorporating Thermal Gel Packs of the present invention
12 therapeutic brassiere
14 thermal gel pack
16 cup member
18 broadband of 12
20 underband of 12
22 shoulder strap of 12
24 open seam of 18
26 hook and loop fastener element of 24
26 pocket element of 16
28 exterior material of 26
30 interior material of 26
32 padded material of 26
34 nipple area
36 thermal gel of 14
38 fluid impervious material of 14
40 semi-circular configuration of 14
42 circular configuration of 14
44 segmented configuration of 14
46 user
48 central recess of 42

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. The present invention 10 is a therapeutic brassiere 12 having thermal gel packs encased within the cup members 16 to provide either heat or cold treatment to the breast area as needed. An open seam 24 in the broadband 18 is selectively engaged and disengaged with hook and loop fastening elements 26 thereby allowing the user 46 to easily put on and remove the garment.

Figure 2:
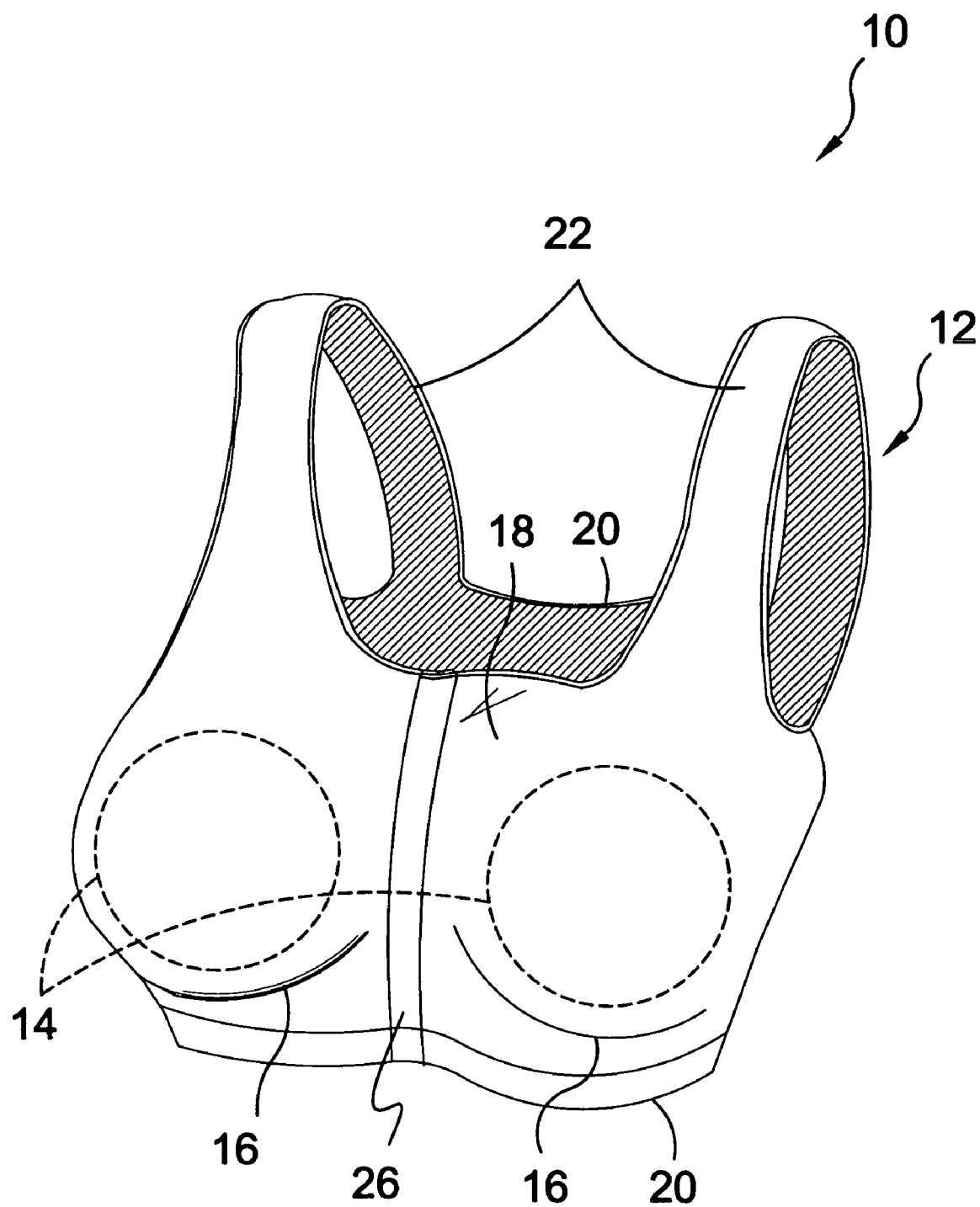
FIG. 2 is a perspective view of the present invention.

FIG. 2 is a perspective view of the present invention 10. The present invention 10 is a therapeutic brassiere 12 with the garment components comprising a broadband 18 with an underband 20 underneath and looping therearound connecting the sides of the broadband 18 and shoulder straps 22 extending from top portions of the broadband 18 to the underband 20. The rear portion of the underband 20 can be high-backed as shown or may more closely be configured as a conventional brassiere. Thermal gel packs 14 are disposed within the cup members 16 of the brassiere. The broadband 18 is divided in the sternum area and selectively engaged with a hook and loop fastening element 26.

Figure 3:
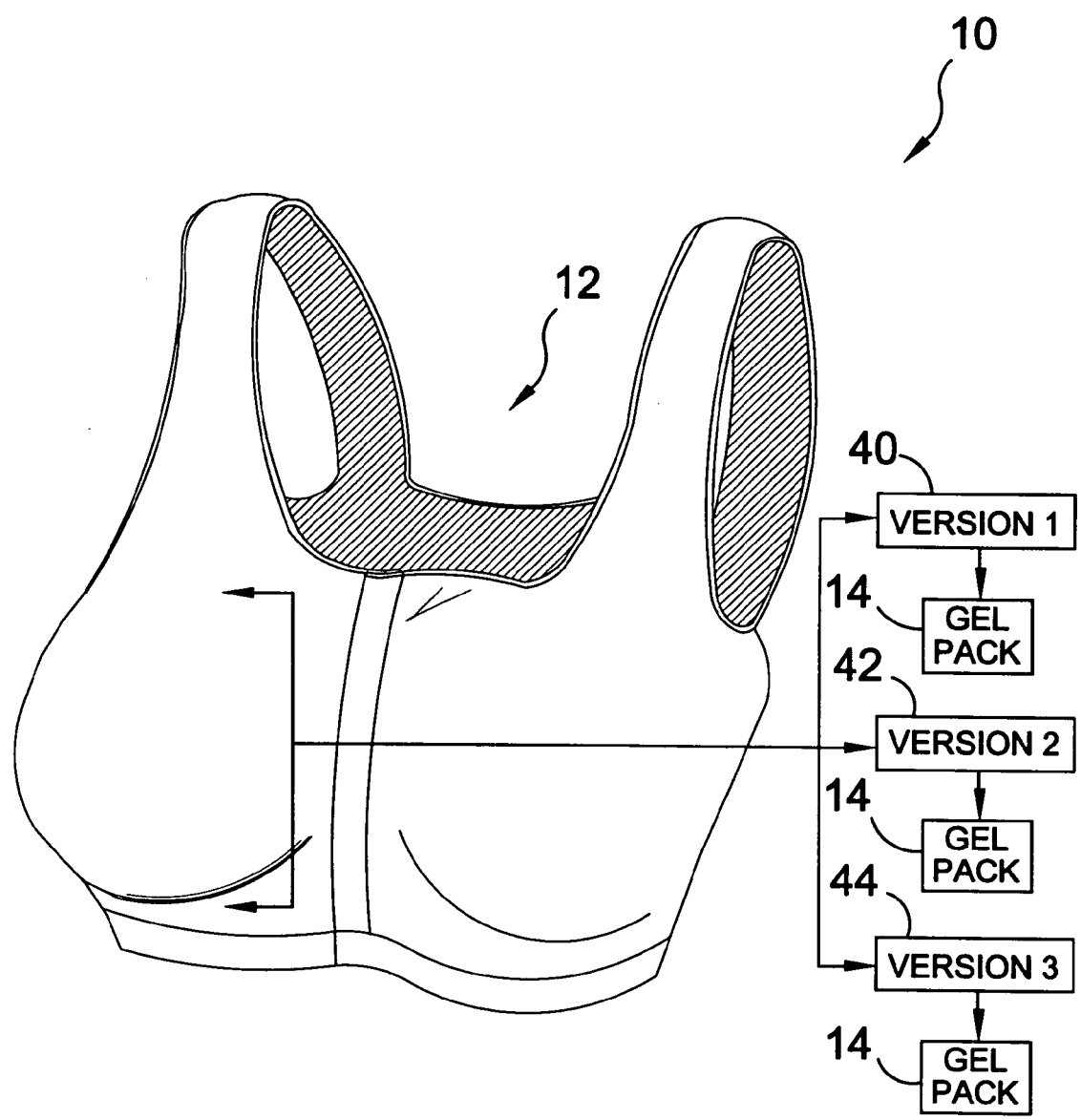
FIG. 3 is a perspective view of the present invention.

FIG. 3 is a perspective view of the present invention 10. Shown is the present invention 10, a therapeutic brassiere 12 designed with integral thermal gel packs 14 that can be in a first semi-circular configuration 40, a second circular configuration 42 and a third segmented configuration 44.

Figure 4:
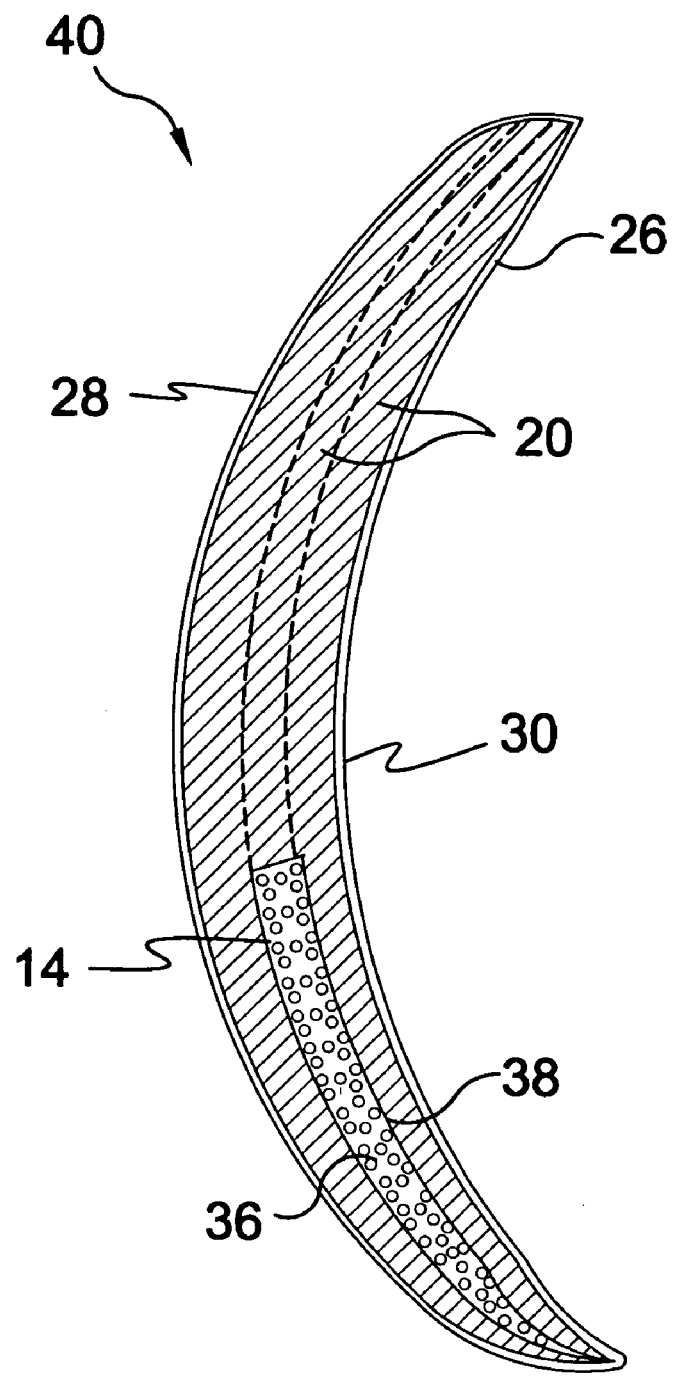
FIG. 4 is a sectional view of the first version of the present invention.

FIG. 4 is a sectional view of the first version 40 of the present invention. Shown is the first version 40 of the present invention having a pocket element 26 defined by an exterior material 28 and an interior material 30 filled with a padded material 32 having a semi-circular gel pack 14 encased therein. The gel pack 14 comprises an envelope of fluid impervious material 38 filled with a non-toxic thermal gel 36 capable of being warmed or chilled as needed and retaining the thermal properties to transfer them to breast area proximal thereto to provide, respectively, heat therapy or cold therapy.

Figure 5:
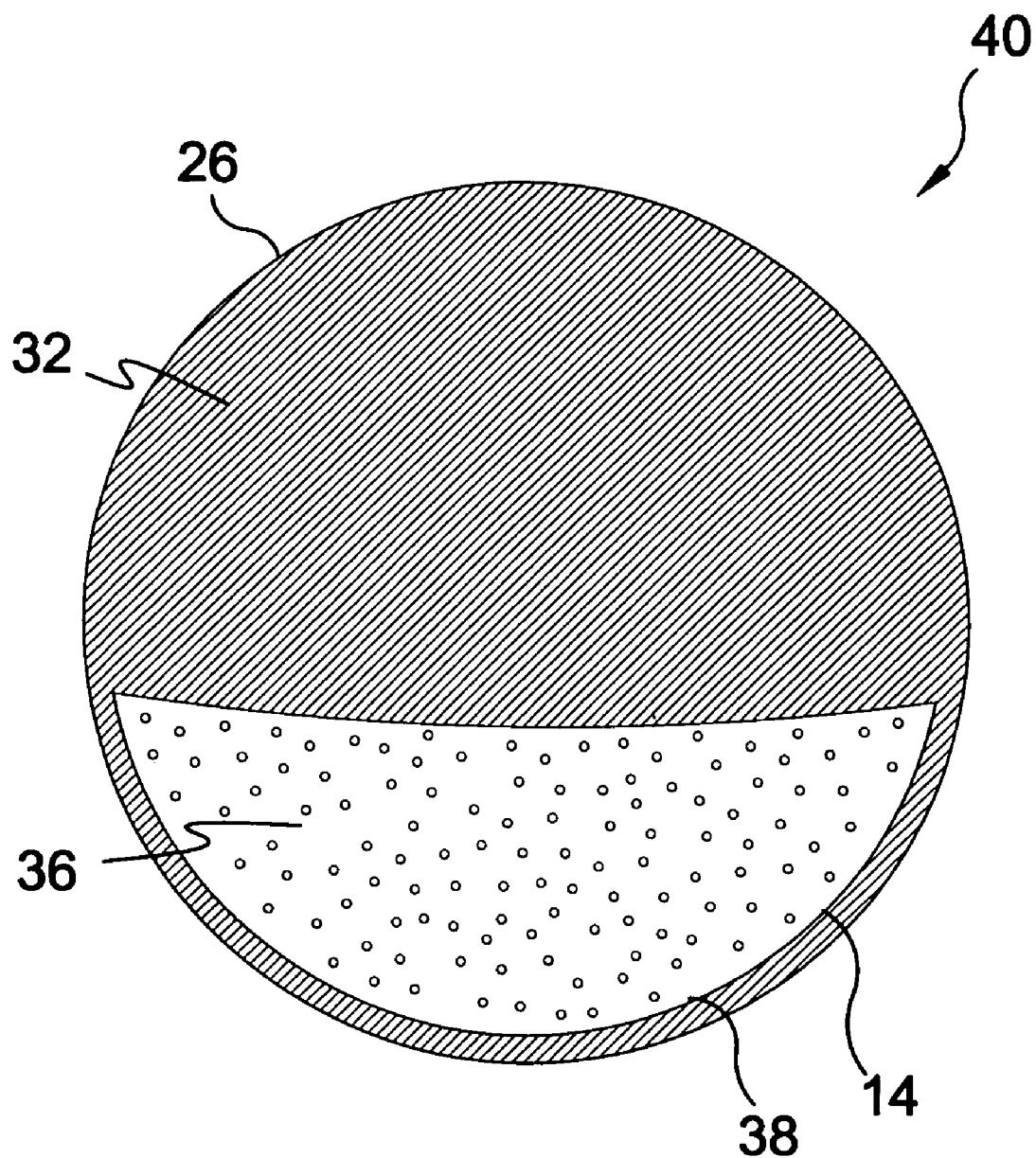
FIG. 5 is a frontal view of the first version of the present invention.

FIG. 5 is a frontal view of the first version 40 of the present invention. Shown is the first version 40 of the present invention, a bra having an inside layer and an outside layer with a thermal gel pack 14 positioned therebetween forming an integral part therewith. Said gel pack 14 comprising a thermal gel 36 encompassed by a fluid impermeable envelope 38. Said envelope 38 manufactured with or without an aperture proximate a breast nipple location. The rest of the pocket 26 is filled with padded material 32.

Figure 6:
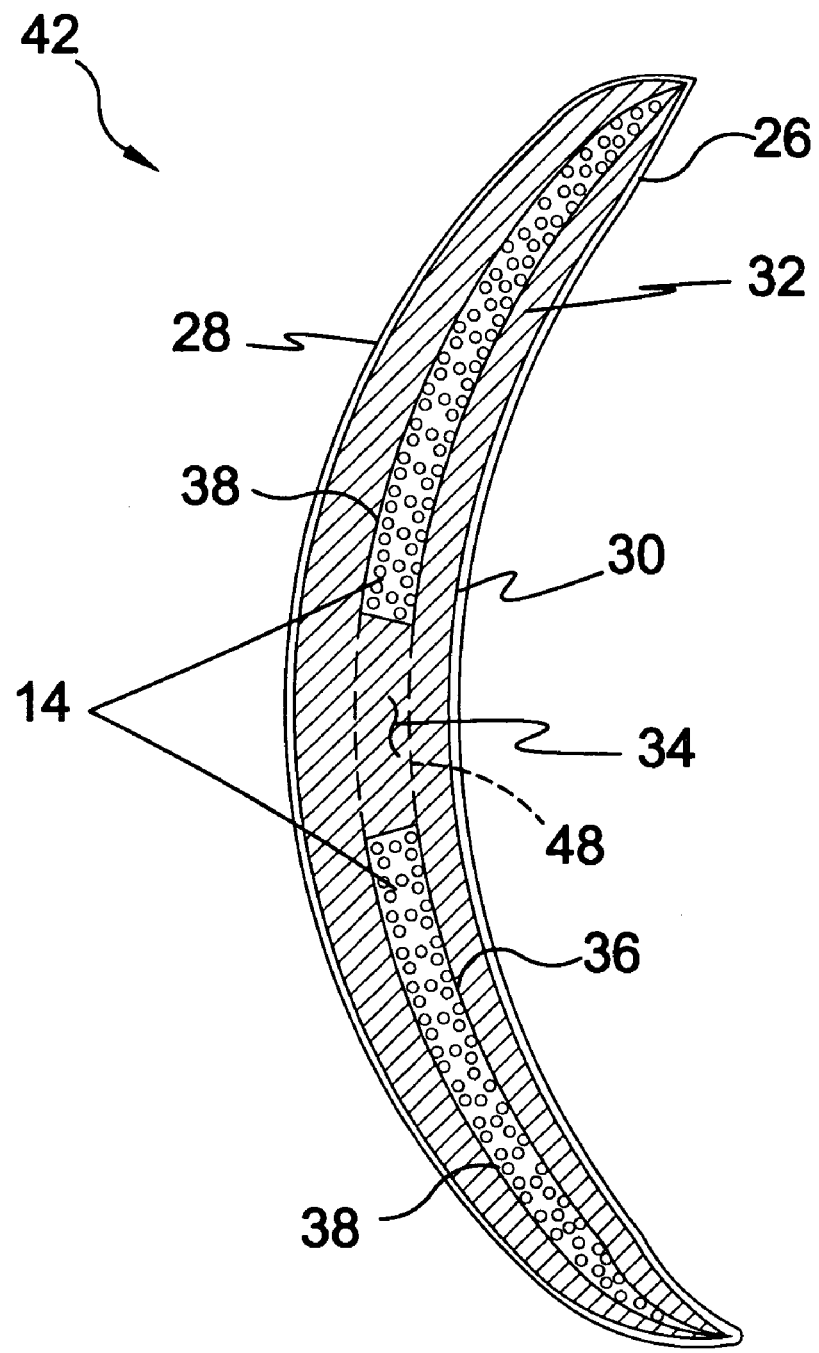
FIG. 6 is a sectional view of the second version of the present invention.

FIG. 6 is a sectional view of the second 42 version of the present invention. Shown is the second version 42 of the present invention having a pocket element 26 defined by an exterior material 28 and an interior material 30 filled with a padded material 32 having a gel pack 14 of a circular configuration 42 encased therein. The gel pack 12 of the second configuration 42 includes a central recess 48 in the nipple area 34. The gel pack 14 comprises an envelope of fluid impervious material 38 filled with a non-toxic thermal gel 36 capable of being warmed or chilled as needed and retaining the thermal properties to transfer them to breast area proximal thereto to provide, respectively, heat therapy or cold therapy.

Figure 7:
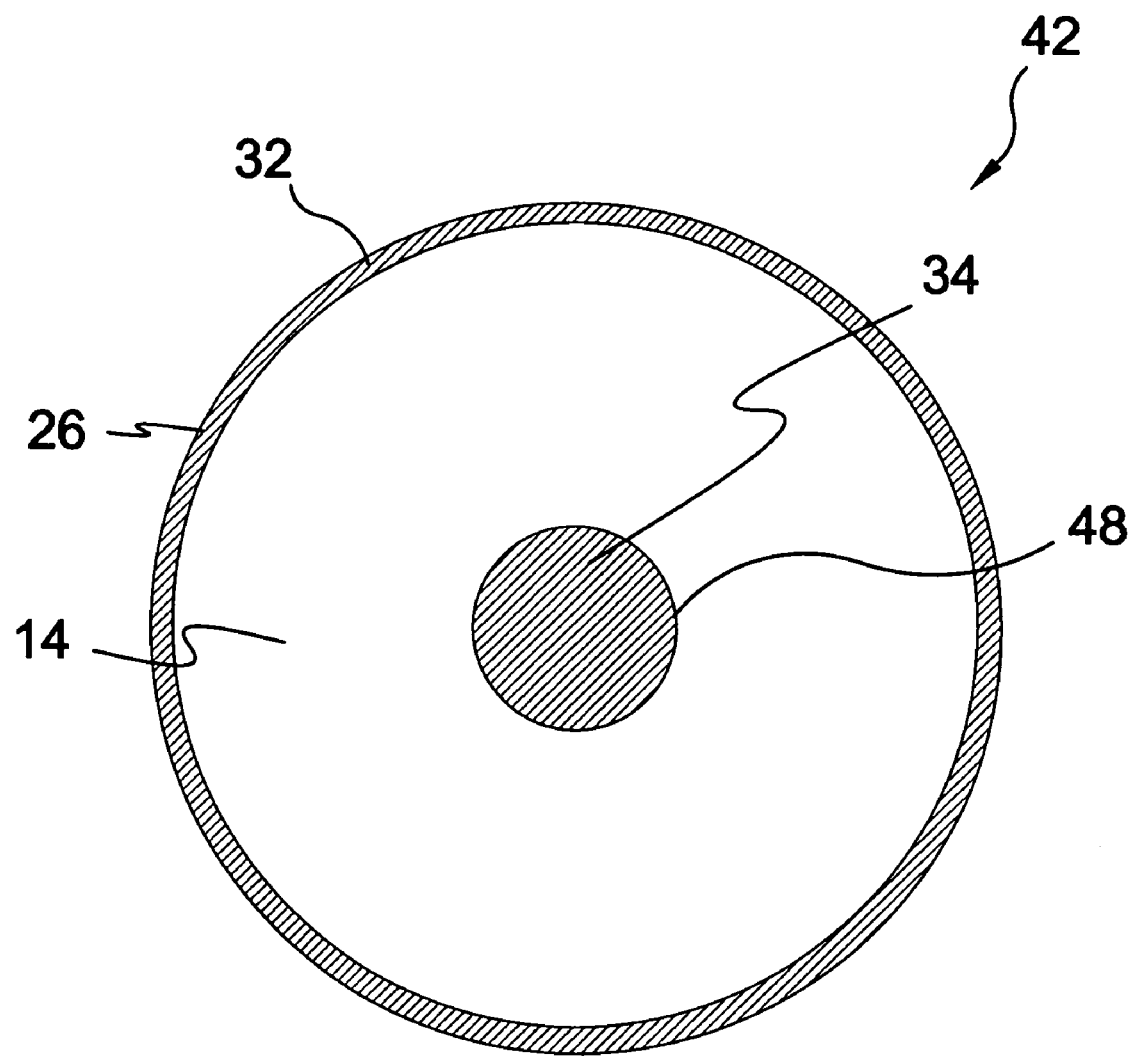
FIG. 7 is a frontal view of the second version of the present invention.

FIG. 7 is a frontal view of the second version 42 of the present invention. Shown is the second version 42 of the present invention, a bra having an inside layer and an outside layer with a thermal gel pack 14 positioned therebetween forming an integral part therewith. Said gel pack 14 comprising a thermal gel encompassed by a fluid impermeable envelope. The circular configuration 42 of the gel pack 14 is manufactured with a central recess 48 proximate a breast nipple location 34. The rest of the pocket 26 is filled with a padded material 32.

Figure 8:
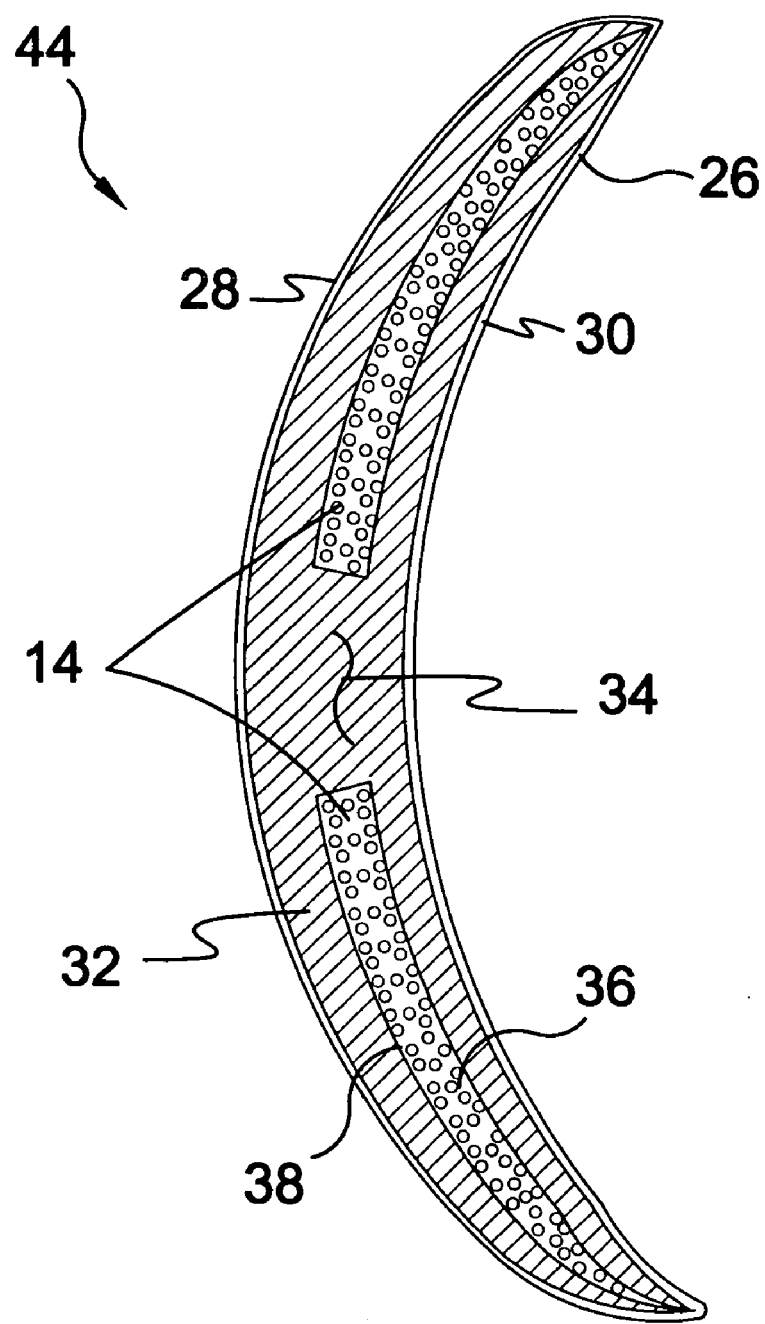
FIG. 8 is a sectional view of the third version of the present invention.

FIG. 8 is a sectional view of the third version 44 of the present invention. Shown is the third version 44 of the present invention having a pocket element 26 defined by an exterior material 28 and an interior material 30 filled with a padded material 32 with a plurality of gel packs 14 in a segmented configuration 44 encased therein. The gel packs 14 of the segmented configuration 42 terminate prior to the nipple area 34. The gel pack 14 comprises an envelope of fluid impervious material 38 filled with a non-toxic thermal gel 36.

Figure 9:
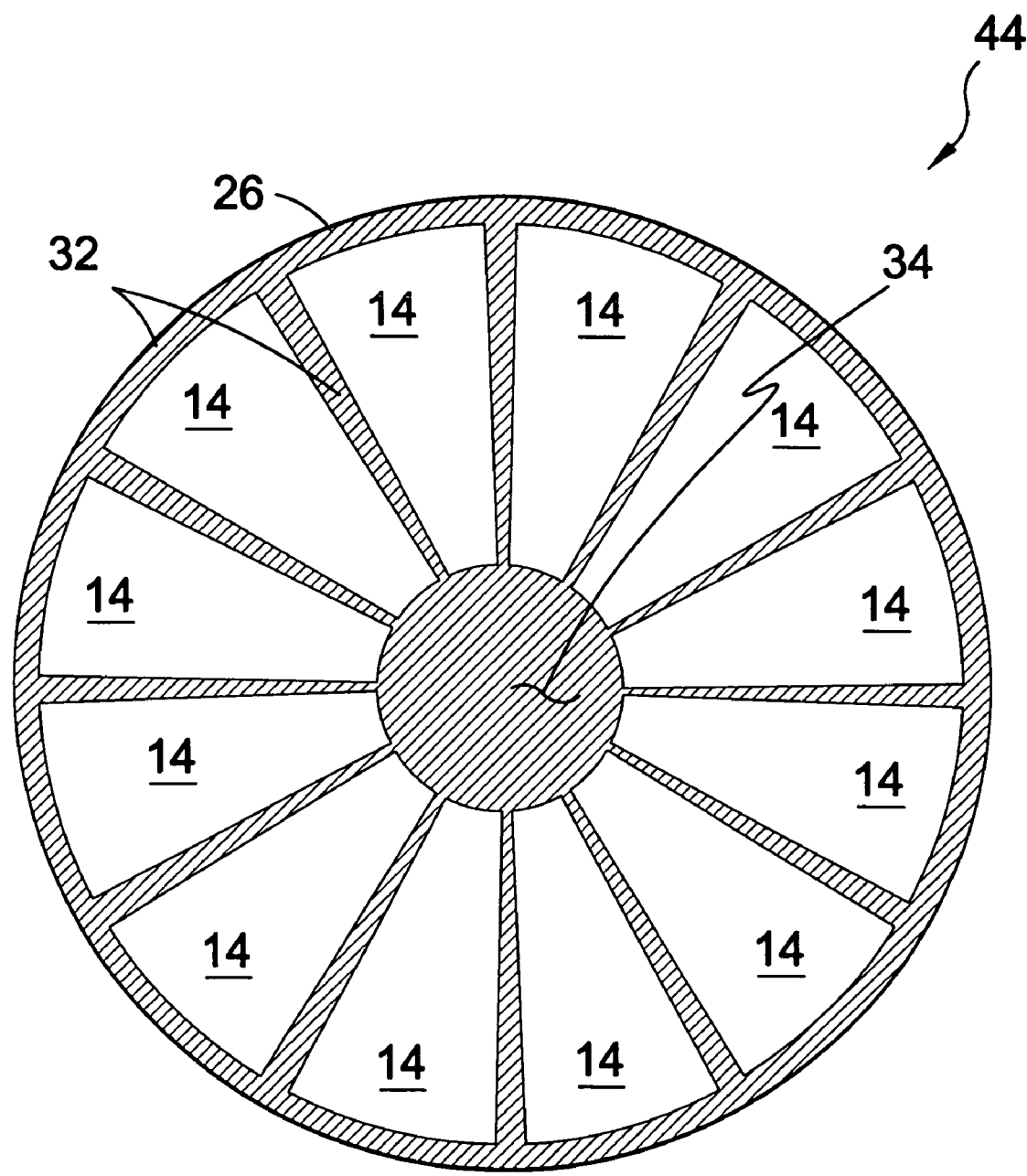
FIG. 9 is a frontal view of the third version of the present invention.

FIG. 9 is a frontal view of the third version 44 of the present invention. A plurality of gel packs 14 are arranged in a circular segmented configuration 44 that leaves the nipple area 34 unexposed to thermal transfer. The rest of the pocket 26 is filled with padded material 32.

Figure 10:
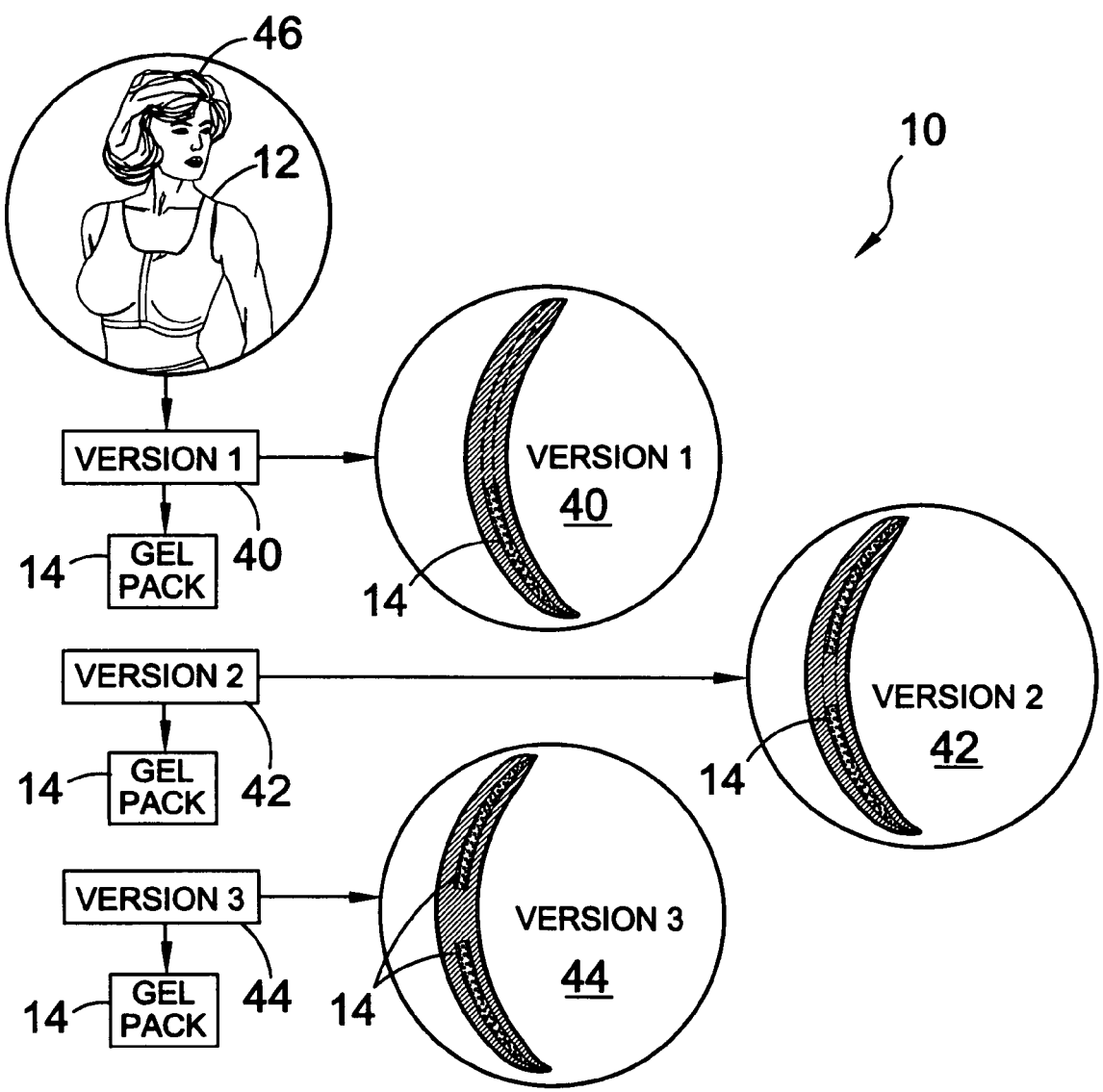
FIG. 10 is a chart view of the present invention.

FIG. 10 is a chart view of the present invention 10. Shown is a chart of the present invention 10, a therapeutic brassiere 12 containing thermal gel packs 14 that can provide either heat therapy of cold therapy to the breast of the user 46. The gel packs 14 have a first semi-circular configuration 40, a second circular configuration 42 and a third segmented configuration 44. All configurations are arranged to avoid thermal transfer to the nipple area.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

What is claimed is new and desired to be protected by Letters Patent is set forth in the appended claims:

1. A therapeutic brassiere incorporating thermal gel packs comprising:
   a) a front broadband having adjacent cup members covering cup areas including nipple areas;
   b) an underband underneath said broadband and forming a loop extending from one side of said broadband to the opposing side thereof;
   c) a pair of opposing shoulder straps extending from a top portion of said broadband to said underband;
   d) an open seam traversing the sternum area of said broadband thereby separating said cup members;

e) mating hook and loop fastener elements disposed on said open seam extending along the length of their respective edges thereby providing a quick and easy means of selectively engaging and disengaging said seam;

f) a pocket disposed integral with each cup member, said pocket formed by a layer of exterior material overlaying a layer of interior material, said pocket substantially covering the cup area;

g) padded material filling each said pocket wherein the central portion is thicker and narrows as it reaches the peripheral edges thereof to provide a smooth transition and a natural aesthetic when worn; and h) a thermal gel pack encased in a gel sac with said padding for each pocket bypassing the area immediately adjacent the nipple area wherein said gel pack can be selectively heated or chilled as needed to retain the appropriate thermal properties for an extended period of time in order to provide thermal therapeutic treatment to a portion of the breast adjacent thereto, said gel sacs being integral parts of said brassiere.

2. A therapeutic brassiere incorporating thermal gel packs as recited in claim 1, wherein said gel packs are limited to areas below the nipple areas thereby configured to bypass the nipple area to prevent thermal transfer thereto.

3. A therapeutic brassiere incorporating thermal gel packs as recited in claim 1, wherein said gel packs are segmented extending radially from a central portion outside the nipple areas and padding material positioned between segments for providing support for said gel sacs.

4. A therapeutic brassiere incorporating thermal gel packs as recited in claim 1, wherein each said gel pack is substantially circular to substantially encompass said breast and includes a centrally positioned recess for said nipple area.

5. A therapeutic brassiere incorporating thermal gel packs as recited in claim 1, wherein said gel pack is encased in a hypoallergenic, fluid impervious material.

6. A therapeutic brassiere incorporating thermal gel packs as recited in claim 5, wherein said thermal gel in said gel pack is non-toxic.

* * * * *